(12) United States Patent
Dalko et al.

(10) Patent No.: US 8,759,331 B2
(45) Date of Patent: Jun. 24, 2014

(54) X-RAY AND GAMMA-PHOTON ACTIVABLE ORGANIC COMPOUNDS, THEIR PREPARATION AND THEIR USES

(75) Inventors: Peter Dalko, Orsay (FR); Morgane Petit, Paris (FR); David Ogden, Rambouillet (FR); Guillaume Bort, Toulouse (FR); Cécile Sicard, Chaville (FR)

(73) Assignees: Centre National de la Recherche Scientifique, Paris (FR); Universite Paris Descartes, Paris (FR)

( * ) Notice: Subject to any disclaimer, the term of this patent is extended or adjusted under 35 U.S.C. 154(b) by 0 days.

(21) Appl. No.: 13/704,495

(22) PCT Filed: Jun. 15, 2011

(86) PCT No.: PCT/IB2011/052595
§ 371 (c)(1),
(2), (4) Date: Mar. 28, 2013

(87) PCT Pub. No.: WO2011/158189
PCT Pub. Date: Dec. 22, 2011

(65) Prior Publication Data
US 2013/0190284 A1    Jul. 25, 2013

(30) Foreign Application Priority Data
Jun. 15, 2010  (EP) .................................... 10290323

(51) Int. Cl.
A61K 31/555    (2006.01)
C07D 403/12    (2006.01)

(52) U.S. Cl.
USPC ......................................... 514/184; 540/465

(58) Field of Classification Search
USPC .......................................... 514/184; 540/465
See application file for complete search history.

(56) References Cited

FOREIGN PATENT DOCUMENTS

WO        2006/051142        5/2006
WO    WO2006/051142    *   5/2006

OTHER PUBLICATIONS

Bungard et al. CAS: 158: 679207, 2013.*

* cited by examiner

Primary Examiner — Rei-tsang Shiao
(74) Attorney, Agent, or Firm — Morgan, Lewis & Bockius LLP

(57) ABSTRACT

The present invention relates to a X-ray and gamma-photon activable compound responding to the following formula (I). The present invention also relates to methods of synthesizing a compound according to the invention, and to an aqueous or physiological solution comprising at least one compound of the invention. The present invention also concerns a method of liberating a biologically active compound, said method involving the step of irradiating at least one compound, or at least one aqueous or physiological solution according to the invention. Finally, the present invention relates to a pharmaceutical composition comprising at least one compound, or at least one aqueous or physiological solution according to the invention.

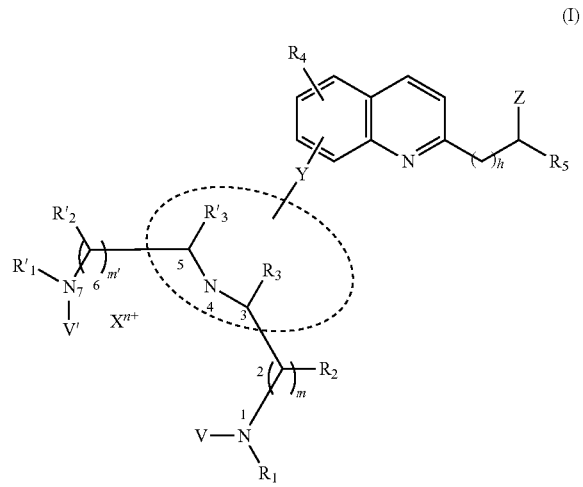

21 Claims, No Drawings

X-RAY AND GAMMA-PHOTON ACTIVABLE ORGANIC COMPOUNDS, THEIR PREPARATION AND THEIR USES

The present invention relates to a X-ray and gamma-photon activable organic compound, to methods of synthesizing such a compound, and to an aqueous or physiological solution comprising at least one compound according to the invention. The present invention also relates to a method of liberating a biologically active compound, said method involving the step of irradiating at least one compound, or at least one aqueous or physiological solution according to the invention. Finally, the present invention relates to a pharmaceutical composition comprising at least one compound, or at least one aqueous or physiological solution according to the invention.

The targeted liberation of biologically active compounds was envisioned for applications in pharmacological sciences. Many creative approaches were devised with more or less success of addressing biologically active compounds in living organisms with minimized side effects. As no general solution was found to this problem, most of the potential of the vectorization remains underexploited.

Among the developed methods, the transformation of a drug to a prodrug is one of the most commonly used strategy. The rationale behind the use of a prodrug is generally guided by absorption, distribution, metabolism, and excretion (ADME) optimization. Additionally, the use of a prodrug strategy increases the selectivity of the drug for its intended target. An example can be seen in many chemotherapy treatments, in which the reduction of adverse effects is always of paramount importance. Some of them (type II prodrugs) are converted to biologically active substrates extracellularly, either in the medium of gastrointestinal (GI) fluids (type IIA), within the systemic circulation and/or other extracellular fluid compartments (type IIB), or near therapeutic target tissues/cells (type IIC), relying on common enzymes, such as esterases and phosphatases or target directed enzymes. The presence of the enzyme is the perquisite of the compound's release in a prodrug strategy. Hence, this vectorization suffers a major drawback as the administered drug spread by passive transport can be activated on its way by activating enzymes that are usually ubiquitously present in the living body, allowing only a small amount of administered prodrug to reach its target. To circumvent this drawback by keeping the drug's efficiency as high as possible, localized liberation of compounds is of course a major challenge.

Light activable conjugates (caged compounds) offer great flexibility in initiating chemical or biochemical events at the nano-scale—hundreds of nanometers—with good time resolution, spatial and time-control (G. C. R. Ellis-Davies, Nature Meth. 2007, 4, 619-628; L. Sjulson et al., Chem. Rev. 2008, 108, 1588-1602; H. M. Lee et al., ACS Chem. Biol. 2009 4, 409-427; A. Specht et al., HFSP Journal 2009, 3, 255-264; G. Mayer et al., Angew. Chem. Int. Ed. 2006, 45, 4900-4921; W. R. Zipfel et al., Nat. Biotechnol. 2003, 2, 1369-1377; M. Matsuzaki et al., Nature 2004, 429, 761-766; H. Kasai et al., Cold Spring Harbor Laboratory Press, New York, 2005, pp. 375-384; R. S. Givens et al., CRC Press, Bocca Raton, 2004, Chapter 69, 1-46). The photochemical external control of in vivo biological process by light is becoming increasingly important in cutting edge biological research. Indeed, photocleavable reagents capable of releasing photolabile compounds quickly upon irradiation are potentially valuable tools, notably for study of biological phenomena. In this case, light-responsive compounds comprise a caging moiety that is linked to a biologically active moiety, said compounds being able to release the active moiety under irradiation. The photorelease compounds, which are temporarily inactive (before the irradiation) can be used therefore to deliver active moieties, like peptides, proteins, nucleic acids or effector molecules ("small molecules"), where their activity is required. Hence, the photolabile protecting groups are removed with light, and the "small molecules" are switched from an inactive state to an active state. Hence, caged compounds are commonly used in molecular biology and in physiological researches for the controlled liberation of a variety of substances. The activity of the biomolecule linked to the caged compound is masked by the photosensitive protecting group, and the light activation (UV or IR light) restores the activity by a process called « uncaging » or « photorelease ». This method is an excellent way to achieve spatial and temporal control over messenger release, and examine the fast kinetics or spatial heterogeneity of biochemical responses in cell or tissue cultures.

Although a wide range of different photolabile protecting groups was developed overall, none of these groups could be activated by X-ray or gamma photon.

Hence, there remains the need of providing photoactivable compounds for use with X-ray or gamma-photon activation, in physiological medium.

Indeed, the use of X-ray activation presents notable advantages over conventional "light window" as X-ray is more penetrating than UV or IR light. As an example, whereas penetrating deepness of UV or IR beams does not exceed 1 mm, significant portion (3.5%) of X-ray photons with energy near 50 keV penetrates a 15-cm-thick tissue. In this way, X-ray controlled liberation of molecules of interest may occur in deep tissues, which open large fields of application in medical sciences. Unfortunately for photo-physical applications, X-ray is "moderately" absorbed by organic systems, a property that is widely exploited in medical imaging while it represents a considerable limitation in the photoactivation of organic compounds.

The inventors have now identified a novel class of caged compounds that responds to a new type of photolysis, using X-ray and gamma-photon activation, and thus allowing the liberation of biologically active compounds in high spatiotemporal control, in basically any media otherwise inaccessible for non-intrusive technique.

The novel compounds of the invention are caged compounds derived from quinoline derivatives tethered via a spacer to a chelating agent such as 1,4,7,10-tetraazacyclododecane-1,4,7,10-tetraacetic acid (DOTA) and derivatives, or DOTA analogs such as 1,4,7-triazacyclononane-N, N',N"-triacetic acid (DO3A) and derivatives, diethylenetriaminepentaacetic acid (DTPA) and derivatives, and pyridine containing triaza-macrocyclic triacetate (PCTA) and derivatives, all of these chelating agents comprising a metal ion.

The compounds of the invention have also considerable advantages in UV and near IR photolysis experiments as they show an excellent solubility in water and also in physiological medium, allowing high spatial and temporal control.

Noteworthy, derivatives of the gadolinium complex are already used as MRI contrast agents for medical diagnostics (P. Caravan et al., Chem. Rev. 1999, 99, 2293-2352), the magnetic properties of Gd(III) allowing the visualization of functional changes in the body. However, the derivatives of Gd(III) were never used to transport, and then release molecules of interest in cells or tissues.

The invention overcomes the inadequacies and disadvantages of the caged compounds of the prior the art by designing original non-toxic caged compounds sensitive to X-ray and gamma-photon, allowing a spatiotemporal controlled release of various drugs in deep tissue by a non-invasive method. More specifically, the compounds of the invention allow an external control of biological processes by light in accordance to non-invasive methodology which produces minimal perturbations of the cellular processes, and with the possibility of spatial and temporal control of drugs activation under in vivo conditions. The compounds of the invention allow the releasing of ligands ("small molecules") acting on intracellular receptors, more particularly under X-ray and gamma-photon sources, said compound presenting higher photorelease sensitivity under a photonic energy ranging from 10 keV to 20 MeV. The compounds of the invention are also water soluble and stable to hydrolysis. The ability to link the substrate to the cage in the late stage of the synthesis represents also a great flexibility that may allow the use of virtually all type of substrates having hydroxyl, phenol, thio, amino, amido, carboxylic or phosphate linking groups. Besides, their photolysis by-products are nontoxic.

The distribution of the caged compound can be directed either by passive transport, or by attaching affinity tags under in vivo conditions. The directed vectorization of the caged conjugates may offer solution not only for the problems of selective targeting of certain cell-types but also may enable extra- or intracellular delivery of selected (caged) drugs. Hence, the compounds of the invention may offer a double control: a selective targeting and a localized activation in deep tissue, which allow a local enhancement of messengers with minimized side effects (for an eventual utilization in medical treatment).

A first subject of the present invention is therefore a novel compound responding to the following formula:

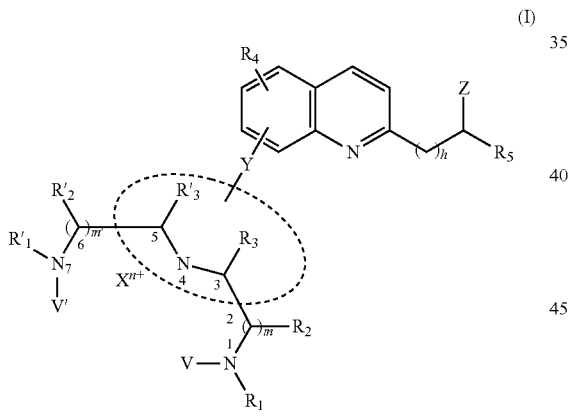

(I)

wherein:
n=2 or 3, and n being preferably equal to 2 when the degree of oxidation of the metal ion is (II) and n being preferably equal to 3 when the degree of oxidation of the metal ion is (III), m and m', identical or different, are equal to 1 or 2, m and m' being preferably equal to 1, h=0 or 1, and h being preferably equal to 0, X is a metal ion, such as a lanthanide selected among Ce(III), Pr(III), Nd(III), Sm(III), Eu(III), Gd(III), Tb(III), Dy(III), Ho(III), Er(III), Tm(III), Yb(III), or a non-lanthanide metal such as Mg(II), Ca(II), Mn(II), Fe(II), Fe(III), Cu(II), Zn(II), Ga(III), In(III), Tl(III), Y(III), Zr(IV), Nb(III), X being preferably a lanthanide, and more preferably a lanthanide selected among Sm(III), Eu(III), Gd(III), Tb(III), Dy(III), Ho(III), and even more preferably Gd(III), V and V', identical or different, are hydrogen atoms, or linear or branched $C_1$-$C_{30}$ alkyl or alkoxy chains, and preferably $C_1$-$C_{10}$ alkyl or alkoxy chains, and more preferably $C_2$ alkyl or alkoxy chains, optionally substituted by one or more groups independently selected among halogen atoms, nitrile, nitro, thio, amino, amido, aryl, heteroaryl, hydroxyl, carboxylic or carboxylate groups, or V and V' are $C_1$-$C_{30}$ alkyl chains, and preferably $C_1$-$C_{10}$ alkyl or alkoxy chains, and more preferably $C_2$ alkyl or alkoxy chains, linked together via a C, O, N or S atom, and preferably N, to form a cycle, said alkyl chains being preferably $C_1$-$C_{10}$ alkyl chains, and more preferably $C_2$ alkyl chains, optionally substituted by one or more groups independently selected among halogen atoms, nitrile, nitro, thio, amino, amido, aryl, heteroaryl, hydroxyl, carboxylic or carboxylate groups, and said C, O, N or S atom being optionally substituted by one or more groups independently selected among hydrogen atoms, or linear or branched $C_1$-$C_{30}$ alkyl or alkoxy chains, and preferably $C_1$-$C_{10}$ alkyl or alkoxy chains, said alkyl or alkoxy chain being optionally substituted by one or more groups independently selected among halogen atoms, nitrile, nitro, thio, amino, amido, aryl, heteroaryl, hydroxyl, carboxylic or carboxylate groups, $R_1$, $R'_1$, $R_2$, $R'_2$, $R_4$ and $R_5$, identical or different, are hydrogen atoms, or linear or branched $C_1$-$C_{30}$ alkyl or alkoxy chains, and preferably $C_1$-$C_{10}$ alkyl or alkoxy chains, said alkyl or alkoxy chains being optionally substituted by one or more groups independently selected among halogen atoms, nitrile, nitro, thio, amino, amido, aryl, heteroaryl, hydroxyl, carboxylic or carboxylate groups, the radical $R_5$ being preferably a hydrogen atom, $R_3$ and $R'_3$, identical or different, are hydrogen atoms, or linear or branched $C_1$-$C_{30}$ alkyl or alkoxy chains, and preferably $C_1$-$C_{10}$ alkyl or alkoxy chains, or $R_3$ and $R'_3$ are linked together to form a heteroalkyl or heteroaryl cycle comprising 5 to 14 atoms, and preferably a pyridine, $R_3$ and $R'_3$ being optionally substituted by one or more groups independently selected among halogen atoms, nitrile, nitro, thio, amino, amido, aryl, heteroaryl, hydroxyl, carboxylic or carboxylate groups, Y is a spacer selected among linear, branched or cyclic $C_1$-$C_{30}$ alkyl or alkoxy chains, and preferably $C_1$-$C_{10}$ alkyl or alkoxy chains, comprising at least one heteroatom selected among O, N and S, and preferably a heterocycle comprising 1 or 2 heteroatoms selected among O, N or S, said spacer Y being directly linked to the quinoline group via its heteroatom O, N or S, and said spacer Y optionally comprising an amido function, and being optionally substituted by one or more groups independently selected among halogen atoms, nitrile, nitro, thio, amino, amido, aryl, heteroaryl, hydroxyl, carboxylic or carboxylate groups, Z is selected among —OH, —OR, —SR, —OC(O)R, —OC(O)OR, —OC(O)NHR, —OC(O)SR, —OC(O)CH(NH$_2$)R, —OC(O)NHCH(COOH)R, —OP(O)(OH)(OH) and —OP(O)(OR)(OR') groups, in which R and R', identical or different, are hydrogen atoms, linear or branched $C_1$-$C_{30}$ alkyl or alkoxy chains, and preferably $C_1$-$C_{10}$ alkyl or alkoxy chains, said alkyl or alkoxy chains being optionally substituted by one or more groups independently selected among halogen atoms, nitrile, nitro, thio, amino, amido, aryl, heteroaryl, hydroxyl, carboxylic or carboxylate groups, or R and R' are optionally substituted aryl or heteroaryl groups comprising 5 to 14 atoms, said aryl groups being optionally substituted by one or more groups independently selected among halogen atoms, nitrile, nitro, thio, amino, amido, aryl, heteroaryl, hydroxyl, carboxylic or carboxylate groups, Z being preferably a —OC(O)R group, in which R is a linear or branched $C_1$-$C_{30}$ alkyl chain, and preferably a $C_1$-$C_{10}$ alkyl chain, and with the proviso that:

the spacer Y is directly linked to one of the carbon atoms $C_3$ or $C_5$ or to the nitrogen atom $N_4$, and when the spacer Y is directly linked to one of the carbon atoms $C_3$ or $C_5$, the nitrogen atom $N_4$ is linked to a radical $R''_1$ selected among hydrogen atom, or a linear or branched $C_1$-$C_{30}$ alkyl or alkoxy chain, and preferably $C_1$-$C_{10}$ alkyl or alkoxy chain, said alkyl or alkoxy chain being optionally substituted by one or more groups independently selected among halogen atoms, nitrile, nitro, thio, amino, amido, aryl, heteroaryl, hydroxyl, carboxylic or carboxylate groups, and when n=2, at least two of the $R_1$, $R'_1$, $R''_1$, $R_2$, $R'_2$, $R_3$, $R'_3$, $R_4$ or Y are substituted by a carboxylate group —COO$^-$, or when n=3, at least three of the $R_1$, $R'_1$, $R''_1$, $R_2$, $R'_2$, $R_3$, $R'_3$, $R_4$ or Y are substituted by a carboxylate group —COO$^-$.

With regard to the compounds known from the prior art, the novel compounds of the invention present the following advantages:

(i) they allow the absorption of a high energy X-ray or gamma-photon, (ii) they can convert the energy of the absorbed X-ray or gamma-photon to lower quanta by a cascade of electron-shell reorganization, and (iii) they may transfer a part of the energy of the absorbed X-ray or gamma-photon to the quinoline group, that undergoes the subsequent fragmentation and liberates the Z—H compound.

The aryl and heteroaryl groups refer to cyclic hydrocarbon aromatic or heteroatomic ring systems having 5 to 14 atoms. Said aryl and heteroaryl groups may be selected among phenyl, furan, pyridine, pyrrole, thiophene, imidazole, pyrazole, oxazole, isoxazole, thiazole, benzene, pyrazine, pyrimidine, pyridazine, benzylcyclobutene, pentalene, benzofurane, isobenzofurane, indole, isoindole, benzothiophene, benzo[c]thiophene, benzimidazole, indazole, benzoxazole, benzisoxazole, benzothiazole, naphthalene, quinoline, isoquinoline, quinoxaline, quinazoline, cinnoline, purine, anthracene or acridine, the preferred aryl groups being phenyl groups.

According to a preferred embodiment, the compound of the invention responds to the following formula:

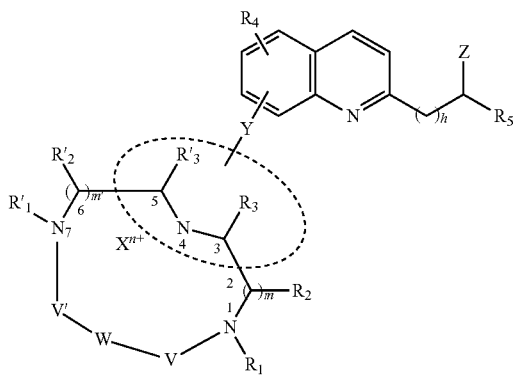

wherein V and V' are optionally substituted linear or branched $C_1$-$C_{30}$ alkyl chains, and preferably $C_1$-$C_{10}$ alkyl chains, and more preferably $C_2$ alkyl chains, linked together via an optionally substituted W atom selected among C, O, N or S to form a cycle, said W atom being preferably a N heteroatom substituted by a $C_1$-$C_{10}$ alkyl or alkoxy chain.

The compound of the invention may respond to one of the following formulas:

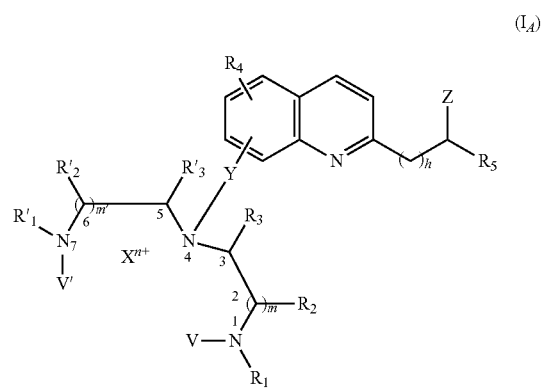

(I$_A$)

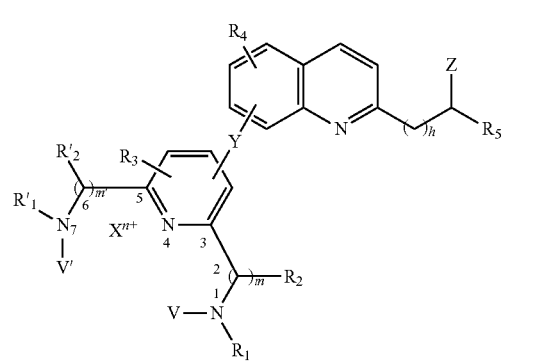

(I$_B$)

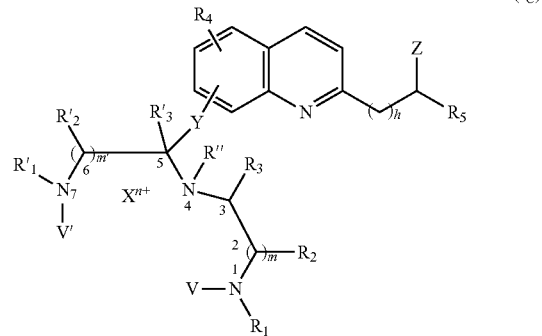

(I$_C$)

According to another preferred embodiment, the spacer Y comprises a heterocycle having 3 to 5 carbon atoms and 1 or 2 heteroatoms selected among O, N or S, and preferably N, said heterocycle being preferably piperazine, piperidine or pyrazoline.

In another preferred embodiment, the spacer Y responds to one of the following formula:

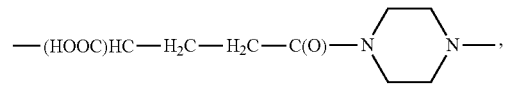

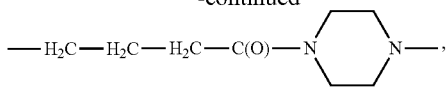

the N heteroatom of said spacer Y being directly linked to the quinoline group.

According to another preferred embodiment, Z is selected among the following groups:

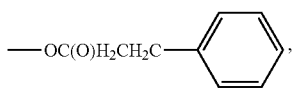

—OC(O)CH₃, —OC(O)CH₂CH₂CH(NH₂)COOH, —OC(O)CH(NH₂)CH₂CH₂COOH.

The invention also relates to a general compound responding to the following formula:

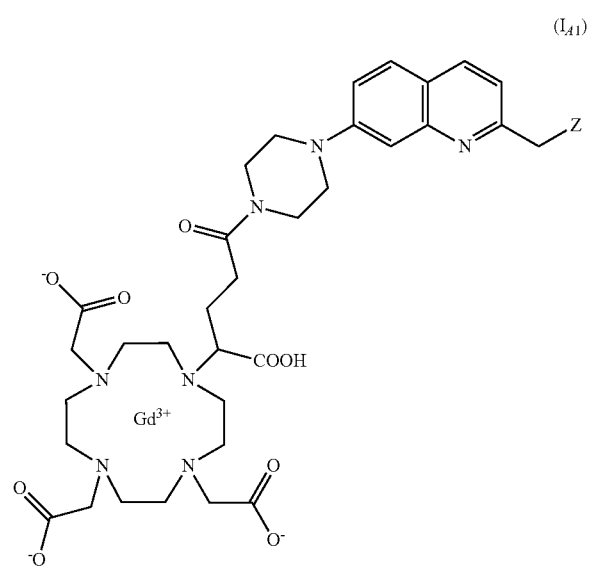

(I$_{A1}$)

wherein Z has the same meaning as defined above.

The compounds of the invention can be synthesized according to a method, which is also part of the invention, comprising the following steps:

(i) transformation of an optionally substituted bromoaniline in a bromoquinaldine, preferably according to the Doebner-Miller reaction conditions described in Vogel's Textbook of Practical Organic Chemistry, Fifth Edition, Longman Scientific Technical, 1989, p. 1187, which is incorporated herewith by reference, (ii) reaction between the bromoquinaldine obtained in step (i) and an amine, such as piperazine, preferably according to the Buchwald-Hartwig reaction conditions described in B. P. Fors et al., J. Am. Chem. Soc., 2009, 131, 5766-5768, and G.

D. Vo, J. Am. Chem. Soc., 2009, 131, 11049-11061, which is incorporated herewith by reference, (iii) amidation of the compound obtained in step (ii) with a protected complex selected among 1,4,7,10-tetraazacyclododecane-1,4,7,10-tetraacetic acid and derivatives, 1,4,7-triazacyclononane-N,N',N''-triacetic acid and derivatives, diethylenetriaminepentaacetic acid and derivatives, pyridine containing triazamacrocyclic triacetate, said complex comprising a metal ion, and (iv) deprotection of the protected functions of the compound obtained in step (iii) with an acid.

The compounds of the invention can also be synthesized according to a method, which is also part of the invention, comprising a peptide coupling reaction between a quinoline derivative at least substituted by a linear, branched or cyclic $C_1$-$C_{30}$ alkyl or alkoxy chain comprising at least one heteroatom selected among O, N or S, said substituent being directly linked to the quinoline group via its heteroatom O, N or S, and said substituent bearing an amino function, with a complex selected among 1,4,7,10-tetraazacyclododecane-1,4,7,10-tetraacetic acid and derivatives, 1,4,7-triazacyclononane-N,N',N''-triacetic acid and derivatives, diethylenetriaminepentaacetic acid and derivatives, or pyridine containing triazamacrocyclic triacetate, said complex comprising a metal ion, and said complex also comprising a carboxylic acid function.

Then, the prepared compounds can be stored as salts, and they can be submitted to a cristallization.

The third object of the invention relates to an aqueous or physiological (plasma) solution comprising at least one compound according to the invention.

Preferably, the compound of the invention is present in said aqueous or physiological composition at a concentration ranging from $10^{-5}$ to 10 mol·L$^{-1}$.

According to another preferred alternative, the aqueous or physiological solution has a pH of 5 to 9.

An additional subject of the invention is an in vivo or in vitro method, and preferably an in vivo method, of liberating a caged substrate (i.e. the Z—H compound), said method comprising the step of irradiating at least one compound, or at least one aqueous or physiological solution as defined according to the invention, and thus releasing the Z—H compound.

The mechanism of liberating the Z—H compound can be schematized according to the following reaction, exemplified on the compound of formula (I$_{A1}$):

Scheme 1

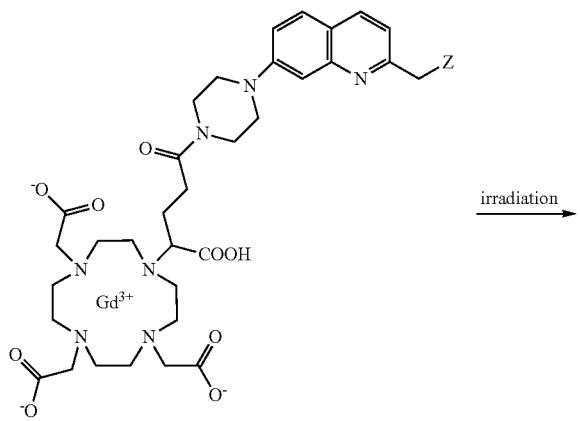

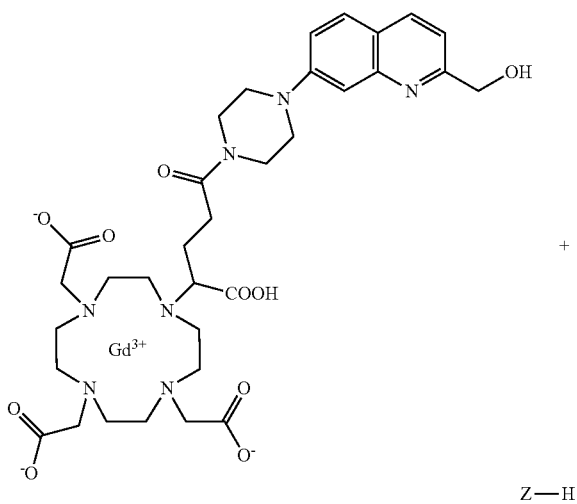

Z—H

The irradiating step of the method of liberating a Z—H compound is preferably carried out under UV, IR, X-ray or gamma irradiation, and preferably under a photonic energy ranging from 10 keV to 20 MeV, and even preferably under a photonic energy ranging from 30 keV to 100 keV. The temperature of irradiation may vary from 0 to 60° C., and preferably the irradiation step is conducted at room temperature (19° C.), or at physiological temperature. The irradiation time depends on the dose rate used and the type of experience, and may vary from ms (millisecond) to 10 hours.

A final object of the invention is a pharmaceutical composition comprising at least one compound or at least one aqueous or physiological solution according to the invention, together with at least one pharmaceutically-acceptable excipient or carrier.

The compound, the aqueous or physiological solution, and the pharmaceutical composition of the invention can be used in a large scale of applications, like biological and medical fields, for the vectorization or targeting or drug delivery of a biologically and/or physiologically active substance of therapeutic interest of formula Z—H, for example into the intercellular space, or more particularly directly in the cells or tissues. In this case, the compound or the aqueous or physiological solution of the invention are injected into the intercellular space, or directly in the cells or tissues of a patient, and then submitted to an irradiating method, as defined above, thus liberating the Z—H compound.

In addition to the above provisions, the invention also comprises other provisions which will become clear from the description which follows, which refers to examples illustrating the advantages of the X-ray and gamma-photon activable compounds of the invention.

EXAMPLES

In this example, the caged compound is a quinoline-derived photocleavable protecting group linked to a compound by a carboxylic function, and that is tethered by a spacer to a Gd(III)-1,4,7,10-tetraazacyclododecane-1-glutaric acid-4,7,10-triacetic acid (DOTAGA) compound (the Gd(III)-DOTAGA group is also named as "antenna sensitizer"), which is a derivative of the Gd(III)-DOTA compound substituted by a glutaric acid as linker.

The X-ray absorption of said compound of formula (I) can be followed by Förster-type energy transfer (Förster T., Ann. Physik, 1948, 437, 55), but it is not the only process possible for the activation, as concurrent mechanism by Raman scattering may occur with or without vibronic enhancement, or by another relevant energy transfer process, that may contribute or eventually may offset the Förster-type process.

Scheme 2

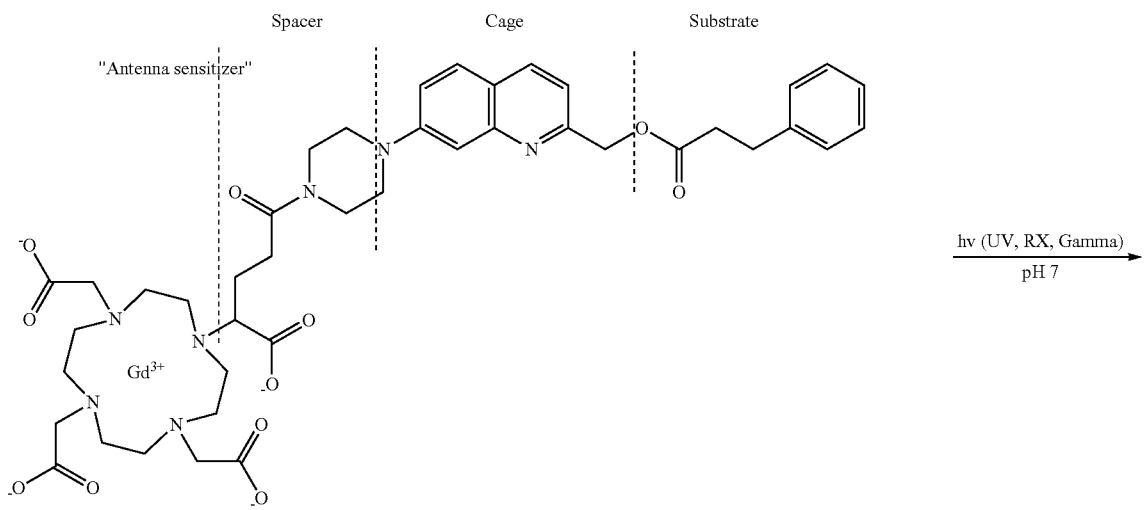

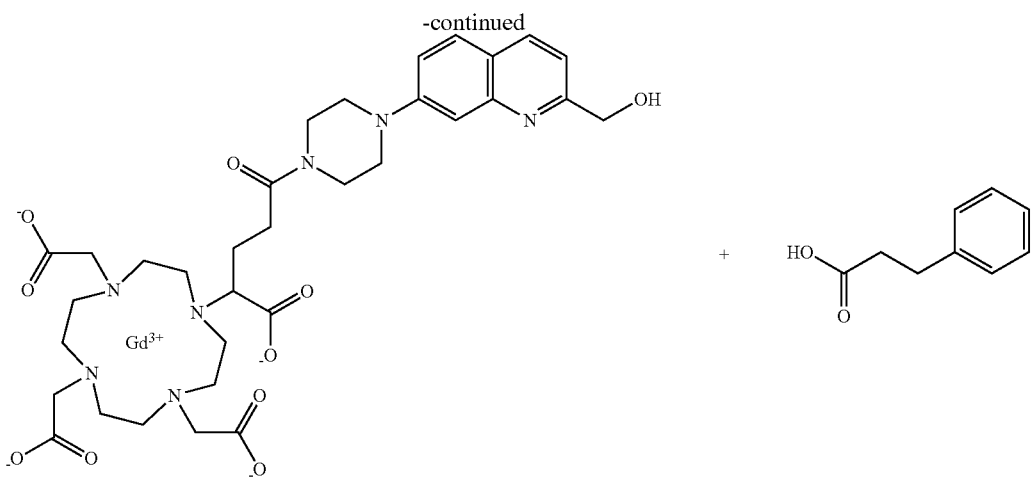

Synthesis of a Gd(III)-DOTA Aminoquinaldine Caged Compound:

The Gd(III)-DOTA aminoquinaldine caged compound of the invention was prepared according to a synthesis following the general Scheme 3. The aminoquinaldine core was prepared by a procedure such as described by Dore et al. (M. Jarrett Davis et al., J. Org. Chem., 2009, 74(4), 1721-1729). According to this protocol the quinaldine core having the key functional elements was prepared by Doebner-Miller synthesis (Vogel's Textbook of Practical Organic Chemistry, Fifth Edition, Longman Scientific Technical, 1989, p. 1187), and the piperazine group was introduced by Buchwald-Hartwig coupling (B. P. Fors et al. J. Am. Chem. Soc., 2009, 131, 5766-5768, and G. D. Vo, J. Am. Chem. Soc., 2009, 131, 11049-11061). After protecting the secondary amino function as a t-butoxycarbamate, the hydroxymethyl side chain was formed by an oxidation-reduction reaction leading to the compound 2. Dihydrocinnamate was selected as model substrate for the photolysis reaction, and was introduced by standard esterification reaction, conducting to the compound 3. The cleavage of the Boc protecting group is followed by an amidation with the Gd(III)-DOTAGA compound in a solvent mixture DMF/H$_2$O 2:1, in the presence of 1-hydroxybenzotriazole (HOBt) hydrate and N-(3-dimethylaminopropyl)-N'-ethylcarbodiimide hydrochloride (EDCI). The desired caged compound 5 was obtained, and then purified by column chromatography on C-18 reverse phase (gradient MeOH/HCO$_2$H 0.05% aq).

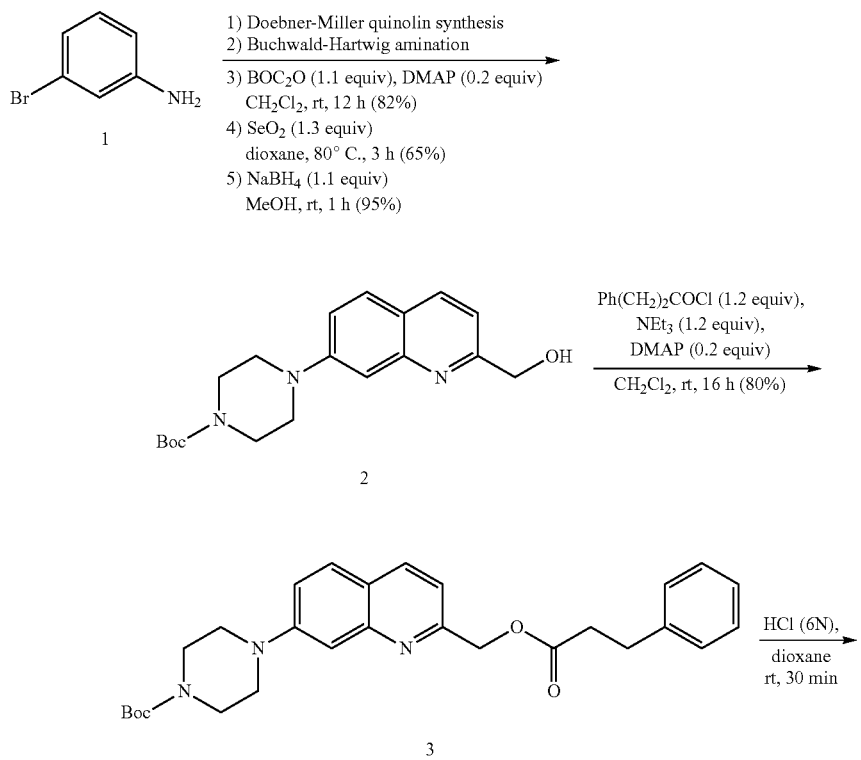

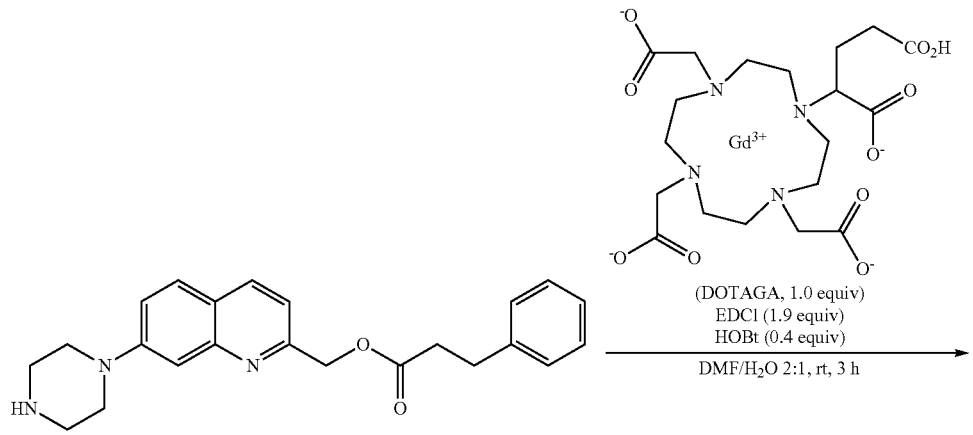

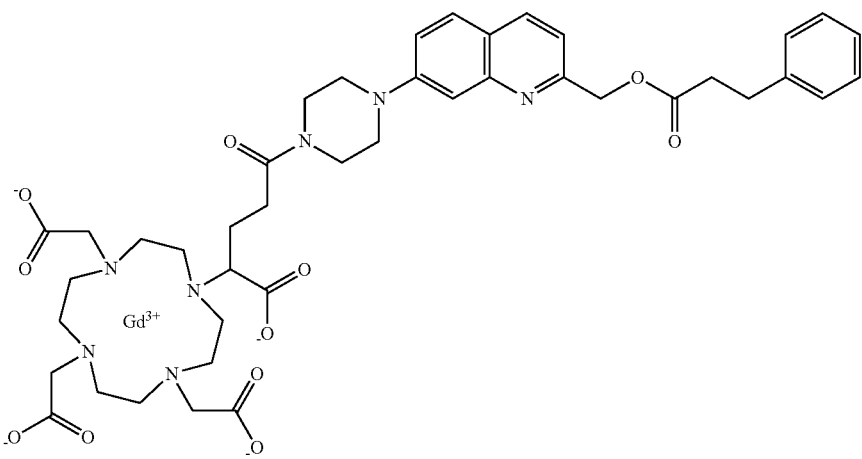

Synthesis of a Metal-DOTA Aminoquinaldine Caged Compound:

According to an alternative method, the metal-DOTA aminoquinaldine caged compound can be prepared as depicted in scheme 4. The aminoquinaldine core was prepared analogously by a procedure such as described by Dore et al. (M. Jarrett Davis et al., J. Org. Chem., 2009, 74(4), 1721-1729). According to this protocol the quinaldine core having the key functional elements was prepared by Doebner-Miller synthesis (Vogel's Textbook of Practical Organic Chemistry, Fifth Edition, Longman Scientific Technical, 1989, p. 1187). The protected hydroxymethylene side-chain was introduced by sequential oxidation-reduction procedure by using $SeO_2$ and $NaBH_4$ in methanol, respectively, and the free hydroxyl group was protected as a silyl ether. As in the previous sequence, the piperazine group was introduced by Buchwald-Hartwig coupling (B. P. Fors et al. J. Am. Chem. Soc., 2009, 131, 5766- 5768, and G. D. Vo, J. Am. Chem. Soc., 2009, 131, 11049-11061), and the protected DOTA analog prepared according to K.-P. Eisenwiener et al. (K.-P. Eisenwiener et al., Bioorg. Med. Chem. Lett. 2000, 10, 2133-2135) was tethered to the piperazine in the presence of 1,3-dimethylaminopropyl-3-ethyl-carbodiimide hydrochloride (EDCI, 1.2 eq) and hydroxybenzotriazol (HOBT, 0.2 eq) as coupling agents. The hydrocinnamate was introduced using dicyclohexylcarbodiimide and dimethylaminopyridine after cleavage of the protected alcohol using tetrabutyl ammonium fluoride (TBAF). Finally the metal complex was formed after the cleavage of the t-butyl protecting groups by using trifluoroacetic acid, and equilibrating the corresponding cavitand by metal-triflate salts (50° C., MeOH, 48 h) (M. P. Placidi et al., J. Am. Chem. Soc., 2009, 131 (29), pp 9916-9917). The desired caged compound 8 was isolated after purification by C-18 reverse phase column chromatography (gradient MeOH/$HCO_2H$ 0.05% aq).

Scheme 4

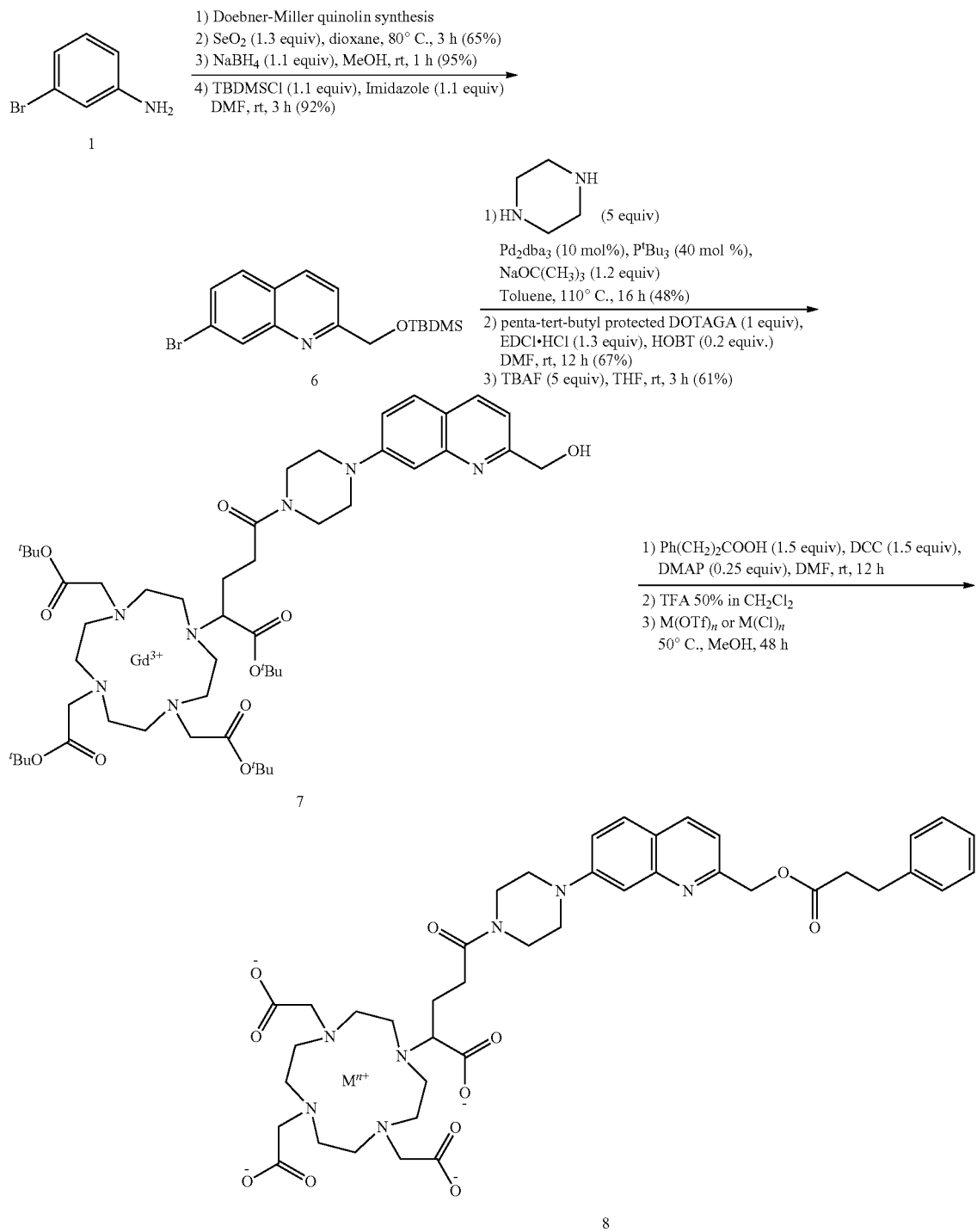

Doebner Miller Synthesis

3-Bromoaniline (10 mL, 92 mmol) was added to a solution of 37% HCl at 0° C. (200 mL). Paraldehyde (11 mL, 0.8 mol, 9 eq) was then introduced and the mixture was left to react at room temperature for 1 hour, and then heated to reflux temperature for 3 hours. After cooling to 0° C., a saturated aqueous solution of sodium hydroxide (200 mL) was slowly added and the mixture was extracted with dichloromethane. The organic layer was washed with water and brine, then dried over $MgSO_4$, and concentrated under reduced pressure. The crude product was obtained as a mixture of 5-bromoquinaldine and 7-bromoquinaldine that were separated by column chromatography ($SiO_2$, cyclohexane-AcOEt 9:1). The 7-bromoquinaldine regioisomer was obtained as a sand yellow solid (9.3 g, 46%).

Molecular formula: $C_{10}H_8BrN$.
Molecular weight: 222.08 g·mol$^{-1}$.
IR (film): 1610, 1494, 1264, 841, 736 cm$^{-1}$.
$T_{fusion}$: 57° C.
$^1$H NMR: δ 8.09 (s, 1H, H$_8$), 7.80 (d, J=8.2 Hz, 1H, H$_4$), 7.39 (m, 2H, H$_5$ et H$_7$), 7.12 (d, J=8.2 Hz, 1H, H$_3$), 2.61 (s, 3H, H$_9$).
$^{13}$C NMR: δ 160.3 (s, C$_2$), 148.6 (s, C$_{8a}$), 136.2 (s, C$_4$), 131.2 (s, C$_8$), 129.4 (s, C$_5$), 128.9 (s, C$_6$), 125.3 (s, C$_{4a}$), 123.7 (s, C$_7$), 122.6 (s, C$_3$), 25.7 (s, C$_9$).

7-Bromoquinoline-2-carbaldehyde Synthesis

Selenium dioxide (1.6 g, 14 mmol, 1.3 eq) was suspended in dioxan (50 mL) and was heated to 60° C. At this temperature 7-bromoquinaldine (2.5 g, 11.2 mmol) was introduced and the mixture was left at 80° C. for 3 hours. After cooling the mixture to room temperature, the crude slurry was filtered on celite, eluted with dioxan and concentrated under reduced pressure. The product was obtained pure as a brown solid (3.3 g, >98%) that was used without furter purification.
Molecular formula: $C_{10}H_6BrNO$.
Molecular weight: 236.06 g·mol$^{-1}$.
IR (film): 1701, 1587, 1298, 911, 843, 757 cm$^{-1}$.
$T_{fusion}$: 151° C.
SM-IC$^+$ (CH$_3$OH) m/z: 236 (M+H$^+$), 268 (hémiacetal), 282 (acetal).

7-Bromoquinoline-2-hydroxymethylene Synthesis

The crude 7-bromoquinoline-2-carbaldehyde (177 mg, 0.75 mmol) was dissolved in EtOH (5 mL) and sodium borohydride (28.4 mg, 0.75 mmol, 1 eq) was then added at 0° C., and the mixture was allowed to room temperature and stirred during 1 hour. The solvent was evaporated under reduced pressure, and then a small amount water was added. The solution was extracted with dichloromethane and the organic layer was washed with water and brine, dried over MgSO$_4$, and concentrated under reduced pressure. The crude alcohol was obtained after purification on silica gel (gradient cyclohexane ethyl acetate) and isolated as a creamy solid (179 mg, >98%).
Molecular formula: $C_{10}H_8BrNO$.
Molecular weight: 238.08 g·mol$^{-1}$.
ESI m/z: 239 (M+H$^+$).

7-Bromo-2-(tert-butyl-dimethyl-silanyloxymethyl)-quinoline Synthesis

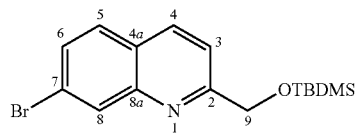

Bromoalcohol (100 mg, 0.4 mmol, 1 eq) was dissolved in DMF (2 mL), and imidazole (31 mg, 0.5 mmol, 1.1 eq) and tert-butyldimethylsilyl chloride (69 mg, 0.5 mmol, 1.1 eq) were added to the medium. After stirring during 5 hours, the mixture was poured into water and extracted twice with cyclohexane. The organic layer was washed with brine, dried over MgSO$_4$, and concentrated under reduced pressure. The product was purified by column chromatography (SiO$_2$, cyclohexane-AcOEt 95:5) and obtained as a white solid (124 mg, 88%).
Molecular formula: $C_{16}H_{22}BrNOSi$.
Molecular weight: 352.34 g·mol$^{-1}$.
$^1$H NMR (500 MHz): δ 8.17 (s, 1H, H$_8$), 8.07 (d, J=8.0 Hz, 1H, H$_4$), 7.68 (d, J=9.0 Hz, 1H, H$_5$), 7.58 (d, J=9.0 Hz, 1H, H$_6$), 7.50 (d, J=8.0 Hz, 1H, H$_3$), 4.97 (s, 2H, H$_9$), 0.97 (s, 9H, $^t$Bu), 0.14 (s, 6H, diMe).
$^{13}$C NMR (500 MHz): δ 164.3 (s, C$_2$), 149.3 (s, C$_{8a}$), 137.8 (s, C$_4$), 132.6 (s, C$_8$), 130.8 (s, C$_5$), 130.2 (s, C$_6$), 127.3 (s, C$_{4a}$), 124.8 (s, C$_7$), 120.2 (s, C$_3$), 68.1 (s, C$_9$), 27.3 (s, 19.8 (s, $^t$Bu), −3.8 (s, diMe).

2-(tert-Butyl-dimethyl-silanyloxymethyl)-7-piperazin-1-yl-quinoline Synthesis

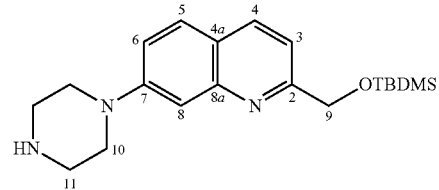

In a sealed tube placed in the glove box, piperazine (613 mg, 7.1 mmol, 5 eq), the bromo derivative (500 mg, 1.4 mmol, 1 eq), Pd$_2$dba$_3$ (145 mg, 0.14 mmol, 10 mol %) and sodium tert-butoxide (161 mg, 1.7 mmol, 1.2 eq) were introduced. A solution of tri-tert-butylphosphine (1 M, 132 μL, 0.56 mmol, 40 mol %) and distilled toluene (5 mL) were added and the tube was sealed. The mixture was heated at 110° C. for 18 hours. After cooling to room temperature, cyclohexane was added, and the organic layer was washed twice with water and brine, dried over MgSO$_4$, and concentrated under reduced pressure. The product was purified by column chromatography (SiO$_2$, dichloromethane-MeOH 9:1) and obtained as an yellow oil (240 mg, 48%).
Molecular formula: $C_{20}H_{31}N_3OSi$.
Molecular weight: 357.57 g·mol$^{-1}$.
$^1$H NMR (500 MHz): δ 7.97 (d, J=8.5 Hz, 1H, H$_4$), 7.60 (d, J=9.0 Hz, 1H, H$_5$), 7.46 (d, J=9.0 Hz, 1H, H$_6$), 7.25 (s, 1H, H$_8$), 7.25 (d, J=8.5 Hz, 1H, H$_3$), 4.94 (s, 2H, H$_9$), 3.28 (t, J=4.5 Hz, 4H, H$_{10}$), 3.03 (t, J=4.5 Hz, 4H, H$_{11}$), 0.95 (s, 9H, $^t$Bu), 0.11 (s, 6H, diMe).
$^{13}$C NMR (500 MHz): δ 163.3 (s, C$_2$), 153.8 (s, C$_7$), 150.3 (s, C$_{8a}$), 137.3 (s, C$_4$), 129.5 (s, C$_5$), 123.2 (s, C$_{4a}$), 120.1 (s, C$_3$), 117.1 (s, C$_6$), 111.8 (s, C$_8$), 68.2 (s, C$_9$), 51.0 (s, C$_{10}$), 47.1 (s, C$_{11}$), 27.3 (s, $^t$Bu), 19.8 (s, $^t$Bu), −3.8 (s, diMe).
ESI m/z: 358 (M+H$^+$)

[4-(1-Acetyl-4-[4-[2-(tert-butyl-dimethyl-silanyloxymethyl)-quinolin-7-yl]-piperazin-1-yl]-4-oxobutyl)-10-butoxycarbonylmethyl-7-(2-oxo-propyl)-1,4,7,10-tetraaza-cyclododec-1-yl]-acetic acid butyl ester Synthesis

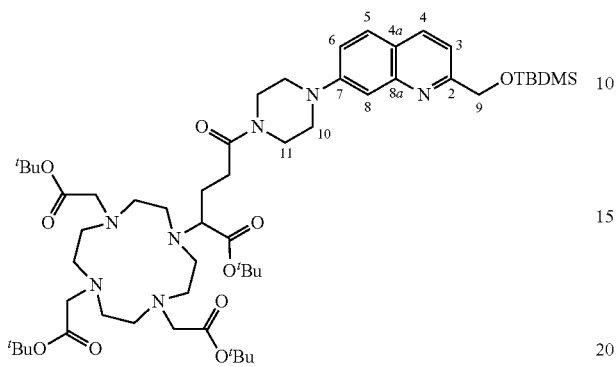

The quinolin derivative (30 mg, 0.08 mmol, 1.7 eq) and the penta-tert-butyl protected DOTAGA (38 mg, 0.05 mmol, 1 eq), were dissolved in DMF. Then, carbodiimide hydrochloride (EDCI.HCl) (14 mg, 0.07 mmol, 1.3 eq) and hydroxybenzotriazole (HOBT) (2 mg, 0.01 mmol, 0.2 eq) were added and the mixture was stirred at room temperature for 16 hours. The solvent was then removed under reduced pressure and the crude product was purified by column chromatography (SiO$_2$, dichloromethane-MeOH 95:5) and obtained as an yellow oil (35 mg, 67%).

Molecular formula: C$_{55}$H$_{93}$N$_7$O$_{10}$Si.
Molecular weight: 1040.45 g·mol$^{-1}$.
$^1$H NMR (500 MHz): δ 7.98 (d, J=8.5 Hz, 1H, H$_4$), 7.63 (d, J=9.0 Hz, 1H, H$_5$), 7.43 (d, J=9.0 Hz, 1H, H$_6$), 7.23 (s, J=8.5 Hz, 1H, H$_3$), 7.18 (s, 1H, H$_8$), 4.87 (s, 2H, H$_9$), 3.28 (t, J=4.5 Hz, 4H, H$_{10}$), 3.03 (t, J=4.5 Hz, 4H, H$_{11}$), 0.89 (s, 9H, $^t$Bu), 0.06 (s, 6H, diMe).
$^{13}$C NMR (500 MHz): δ 176.5 (s, COamide), 174.2 (s, COester), 172.0 (s, COester), 163.5 (s, C$_2$), 152.9 (s, C$_7$), 150.1 (s, 137.5 (s, C$_4$), 129.9 (s, C$_5$), 123.5 (s, C$_{4a}$), 120.4 (s, C$_3$), 117.5 (s, C$_6$), 112.1 (s, C$_8$), 68.2 (s, C$_9$), 51.0 (s, C$_{10}$), 47.1 (s, C$_{11}$), 27.3 (s, $^t$Bu), 19.7 (s, $^t$Bu), −3.9 (s, diMe).
ESI m/z: 1062 (M+Na$^+$).

5-[4-(2-Hydroxymethyl-quinolin-7-yl)-piperazin-1-yl]-oxo-2-(4,7,10-tris-tert-butoxycarbonylmethyl-1,4,7,10-tetraaza-cyclododec-1-yl)-pentanoic acid tert-butyl ester Synthesis

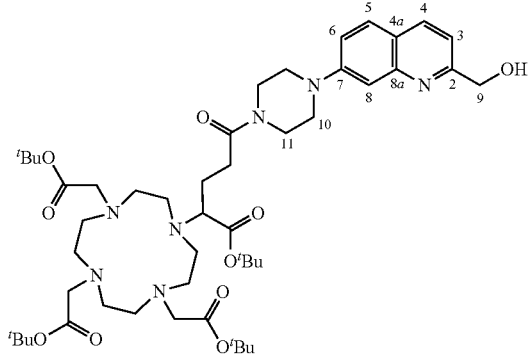 [SMILES: CC(C)(C)OC(=O)CN1CCN(CC(=O)OC(C)(C)C)CCN(C(CCC(=O)N2CCN(c3ccc4ccc(CO)nc4c3)CC2)C(=O)OC(C)(C)C)CCN(CC(=O)OC(C)(C)C)CC1]

The protected alcohol derivative (35 mg, 0.03 mmol, 1 eq) was dissolved in distilled THF. To the mixture was then added a solution of tetra-n-butylammonium fluoride (TBAF) (1 M in THF, 168 μL) and the medium was stirred at room temperature for 3 hours. After concentrated under reduced pressure, the crude product was purified by column chromatography (SiO$_2$, dichloromethane-MeOH 95:5) and obtained as an yellow oil (19 mg, 61%).

Molecular formula: C$_{49}$H$_{79}$N$_7$O$_{10}$.
Molecular weight: 926.19 g·mol$^{-1}$.
$^1$H NMR (500 MHz): δ 7.94 (d, J=8.5 Hz, 1H, H$_4$), 7.65 (d, J=9.0 Hz, 1H, H$_5$), 7.25 (s, 1H, H$_8$), 7.23 (d, J=9.0 Hz, 1H, H$_6$), 7.13 (s, 1H, H$_3$), 4.81 (s, 2H, H$_9$), 3.28 (t, J=4.5 Hz, 4H, H$_{10}$), 3.03 (t, J=4.5 Hz, 4H, H$_{11}$).
$^{13}$C NMR (500 MHz): δ 176.6 (s, COamide), 174.3 (s, COester), 172.1 (s, COester), 161.2 (s, C$_2$), 153.1 (s, C$_7$), 149.7 (s, C$_{8a}$), 137.6 (s, C$_4$), 129.9 (s, C$_5$), 123.5 (s, C$_{4a}$), 120.3 (s, C$_3$), 117.5 (s, C$_6$), 112.2 (s, C$_8$), 68.2 (s, C$_9$), 51.0 (s, C$_{10}$), 47.1 (s, C$_{11}$). ESL m/z: 948 (M+Na$^+$).

5-Oxo-5-[4-[2-(3-phenyl-propionyloxymethyl)-quinolin-7-yl]-piperazin-1-yl]-piperazin-1-yl]-2-(4,7,10-tris-tert-butoxycarbonylmethyl-1,4,7,10-tetraaza-cyclododec-1-yl)-pentanoic acid tert-butyl ester Synthesis

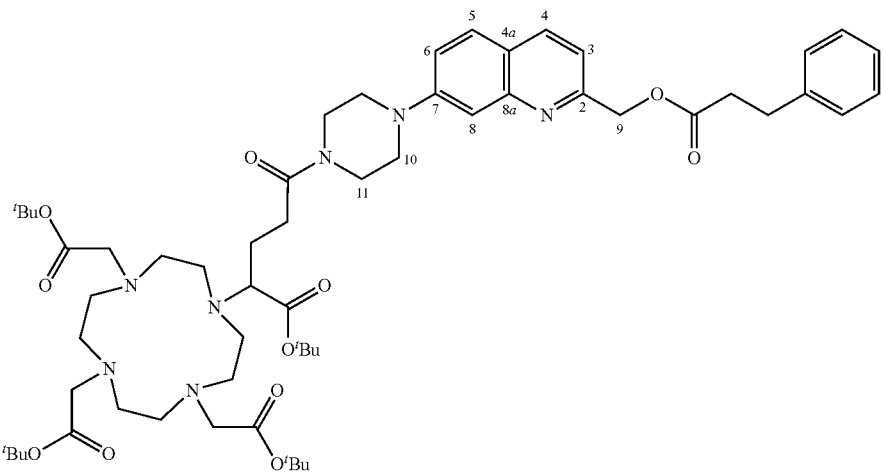 [SMILES: CC(C)(C)OC(=O)CN1CCN(CC(=O)OC(C)(C)C)CCN(C(CCC(=O)N2CCN(c3ccc4ccc(COC(=O)CCc5ccccc5)nc4c3)CC2)C(=O)OC(C)(C)C)CCN(CC(=O)OC(C)(C)C)CC1]

The free alcohol (160 mg, 0.18 mmol), dihydrocinnamic acid (50 mg, 0.35 mmol, 2 eq), DCC (72 mg, 0.35 mmol, 2 eq) and DMAP (10 mg, 0.25 mmol, 0.75 eq) were dissolved in distilled dichloromethane (1 mL) and the mixture was stirred at room temperature for 16 h in the dark. The crude product was purified by column chromatography (SiO$_2$, dichloromethane-MeOH 98:2) and was isolated as an yellow oil (66 mg, 61%).

Photolysis and Radiolysis Experiments:

Then, the photolysis and radiolysis of the compounds of the invention under UV, X-ray and gamma-photon conditions was studied.

without antenna sensitizers are prone to photolysis by using near UV irradiation (366 nm). In contrast, compound 4 was inert under UV irradiation at 366 nm.

When the caged compounds 3 and 4 without the antenna sensitizers were submitted to X-ray irradiation (17.5 keV) no detectable photo-fragmentation were observed. In turn, when the antenna-sensitized compound 5 was submitted to soft X-ray irradiation (17.5 keV) a clean photo-fragmentation occurred, as summarized by Scheme 5. Likewise, when the compound 5 was submitted to hard gamma-ray irradiation (1.17 MeV), a clean photo-fragmentation was observed.

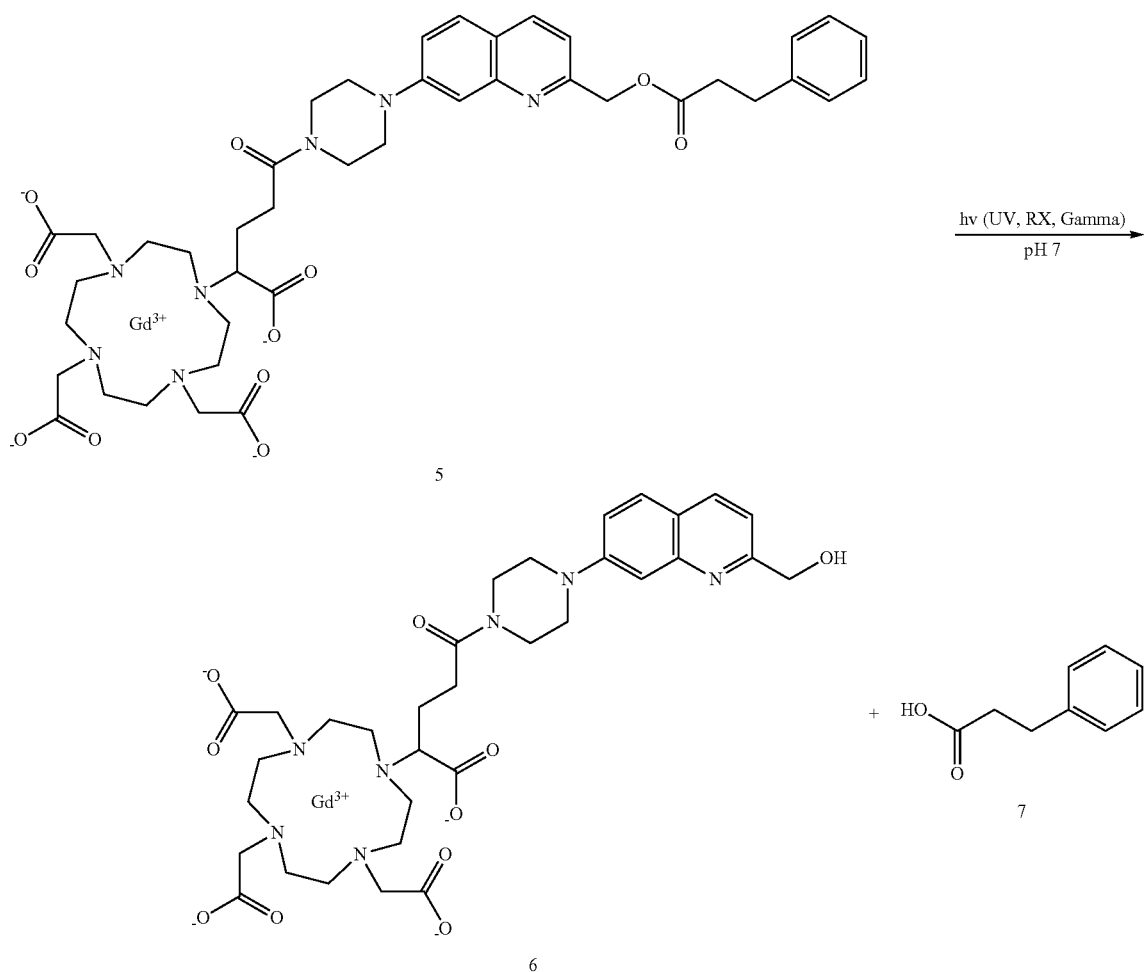

Scheme 5

The photochemical efficiency of any chromophores is determined by the extinction coefficient ($\epsilon$) and the quantum yield ($Q_u$) that is characteristic of the observed photochemical event of the chromophore. The product of these quantities ($\epsilon Q_u$) characterizes the efficiency of the event such as fluorescence or chemical transformation, for example by the incident light.

The photolysis at 366 nm of compound 5 was monitored by the disappearance of the caged hydrocinnamate 5 and by the appearance of the compounds 6 and 7, by using liquid chromatography (LC) or liquid-chromatography-mass spectrometry (LC-MS) techniques. It was shown that the aminoquinoleines 3 and 5 under physiological conditions with or The radiolysis was followed either by the diminution of the caged compound 5, or by the increasing of the photo-products 6 and 7. Under the conditions used, the X-ray radiolysis of the caged compounds appears with a half life of uncaging of 2.5 hours. The photo-fragmentation follows a first order kinetic with a time constant of $4.7 \times 10^{-3}$ min$^{-1}$.

Three types of control have been performed:

(i) the hydrolytic stability of the ester caged compound in TRIS buffer (pH 7 at room temperature (rt)) has been investigated, revealing no notable degradation of the product within four days, and hence attributing the substrate release to the photolysis process, (ii) the caged compounds 3 and 4 missing the Gd(III)-DOTAGA sensitizer antenna have been irradiated under the same conditions, but afforded no traces of photo-fragmentation, (iii) piperazine was transformed to the corresponding N-Boc amide (i.e. to a compound in which the sensitizer antenna was replaced by a Boc group), and the obtained caged structure was submitted to UV and X-ray photolysis respectively. As photolysis was observed under 366 nm irradiation, no appearance of photo-product was observed after submitting the sample to X-ray at 17.5 keV irradiation.

The prepared X-ray sensitive caged compound of the invention presents an absorption maxima at 340 nm for an extinction coefficient $\epsilon_{340\,nm}$=3500 M$^{-1}$·cm$^{-1}$.

Noteworthy, the prepared caged compound undergoes photo-fragmentation by irradiation at 366 nm UV light, in an aqueous buffer solution at pH=7. As the metal complex sensitized cage is highly water-soluble, such compounds offer a good solution to the often encountered solubility problem of the "all-organic" cages.

A) Evaluation of the Compounds of the Invention Under One-Photon (UV) Irradiation Conditions Samples were prepared in c=0.1 mM concentration in aqueous TRIS buffer (pH=7). An aliquot (1 mL) of this solution was irradiated at 366 nm ($\epsilon_{366}$=3000 M$^{-1}$·cm$^{-1}$) in a 1 mL quartz cuvette. The evolution of the photolysis was followed by HPLC using C-18 reverse phase chromatography (XTerra, eluents: methanol/HCO$_2$H (0.1% aq), H$_2$O/HCO$_2$H (0.1% aq) detection at 260 and 320 nm).

The results obtained are the following:
$\lambda_{max}$=340 nm,
$\epsilon(\lambda_{max})$=3500 M$^{-1}$·cm$^{-1}$,
$\epsilon_{366\,nm}$=3000 M$^{-1}$·cm$^{-1}$,
$Q_u$ (366 nm)=0.02,
$\epsilon Q_u$ (366 nm)=60.

B) Evaluation of the Compounds of the Invention Under X-Ray Irradiation Conditions Samples were prepared in c=0.4 mM concentration in aqueous TRIS buffer (pH=7), and 30 µL were irradiated as follows in a plastic cuvette by a 17.5 KeV X-ray source whose calibration according to a Fricke dosimetry (Sprinks J W T, Woods R J 1990, Introduction to Radiation Chemistry, Third Edition, Wiley Interscience) revealed an average dose of 21 Gy/min. The evolution of the radiolysis was followed by HPLC using C-18 reverse phase chromatography (XTerra, eluents: methanol/HCO$_2$H (0.1% aq), H$_2$O/HCO$_2$H (0.1% aq) detection at 260 and 320 nm).

The results obtained are depicted in the following Table 1:

TABLE 1

| Dose (Gy) | % of compound 5 |
|---|---|
| 0 | 92.7 |
| 420 | 78.7 |
| 840 | 70.0 |
| 1260 | 61.1 |
| 1680 | 51.0 |

C) Evaluation of the Compounds of the Invention Under Gamma-Photon Irradiation Conditions Samples were prepared in c=0.4 mM concentration in aqueous TRIS buffer (pH=7), and 30 µL were irradiated as follows in a plastic cuvette by a 1.17 MeV gamma source whose calibration (Fricke dosimetry) revealed an average dose of 28 Gy/min. The evolution of the photolysis was followed by HPLC using C-18 reverse phase chromatography (XTerra, eluents: methanol/HCO$_2$H (0.1% aq), H$_2$O/HCO$_2$H (0.1% aq) detection at 260 and 320 nm).

The results obtained are depicted in the following Table 2.

TABLE 2

| Dose (Gy) | % of compound 5 |
|---|---|
| 0 | 100 |
| 330 | 88.5 |
| 440 | 80.6 |
| 660 | 82.8 |
| 990 | 73.6 |
| 1320 | 64.3 |

These experiments push forward the attractive possibility to perform soon highly controlled release of drugs in deep tissue, by focalized high energy beams.

The invention claimed is:

1. A compound characterized in that it responds to the following formula:

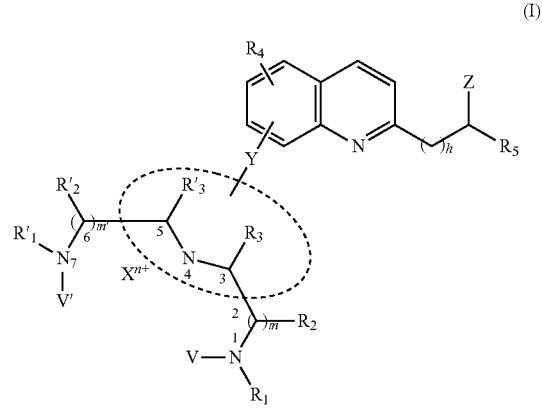

(I)

wherein:
n=2 or 3,
m and m', identical or different, are equal to 1 or 2,
h=0 or 1,
X is a metal ion,
V and V', identical or different, are hydrogen atoms, or optionally substituted linear or branched C$_1$-C$_{30}$ alkyl or alkoxy chains, or optionally substituted C$_1$-C$_{30}$ alkyl chains linked together via an optionally substituted C, O, N or S atom, to form a cycle,
R$_1$, R'$_1$, R$_2$, R'$_2$, R$_4$ and R$_5$, identical or different, are hydrogen atoms, or optionally substituted linear or branched C$_1$-C$_{30}$ alkyl or alkoxy chains,
R$_3$ and R'$_3$, identical or different, are hydrogen atoms, or optionally substituted linear or branched C$_1$-C$_{30}$ alkyl or alkoxy chains, or R$_3$ and R'$_3$ are linked together to form an optionally substituted heteroalkyl or heteroaryl cycle comprising 5 to 14 atoms, and preferably a pyridine,
Y is a spacer selected among optionally substituted linear, branched or cyclic C$_1$-C$_{30}$ alkyl or alkoxy chains comprising at least one heteroatom selected among O, N and S, said spacer Y being directly linked to the quinoline group via its heteroatom O, N or S,
Z is selected among —OH, —OR, —SR, —OC(O)R, —OC(O)OR, —OC(O)NHR, —OC(O)SR, —OC(O)CH(NH$_2$)R, —OC(O)NHCH(COOH)R, —OP(O)(OH)(OH) and —OP(O)(OR)(OR') groups, in which R and R', identical or different, are hydrogen atoms, optionally substituted linear or branched $C_1$-$C_{30}$ alkyl or alkoxy chains, or optionally substituted aryl or heteroaryl groups comprising 5 to 14 atoms, and with the proviso that:

the spacer Y is directly linked to one of the carbon atoms $C_3$ or $C_5$ or to the nitrogen atom $N_4$, and when the spacer Y is directly linked to one of the carbon atoms $C_3$ or $C_5$, the nitrogen atom $N_4$ is linked to a radical $R''_1$ selected among hydrogen atom, or an optionally substituted linear or branched $C_1$-$C_{30}$ alkyl or alkoxy chain, and when n=2, at least two of the $R_1$, $R'_1$, $R''_1$, $R_2$, $R'_2$, $R_3$, $R'_3$, $R_4$ or Y are substituted by a carboxylate group —COO⁻, or when n=3, at least three of the $R_1$, $R'_1$, $R''_1$, $R_2$, $R'_2$, $R_3$, $R'_3$, $R_4$ or Y are substituted by a carboxylate group —COO⁻.

2. A compound as defined according to claim 1, wherein V and V' are optionally substituted linear or branched $C_1$-$C_{30}$ alkyl chains linked together via an optionally substituted C, O, N or S atom, to form a cycle, said compound responding to the following formula:

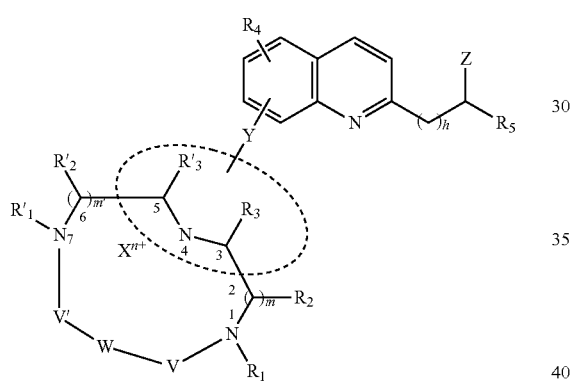

(I₁)

wherein W=C, O, N or S.

3. A compound as defined according to claim 2, wherein V and V' are $C_2$ alkyl chains, and W is a N heteroatom substituted by a $C_1$-$C_{10}$ alkyl or alkoxy chain.

4. A compound as defined according to claim 1, responding to one of the following formulas:

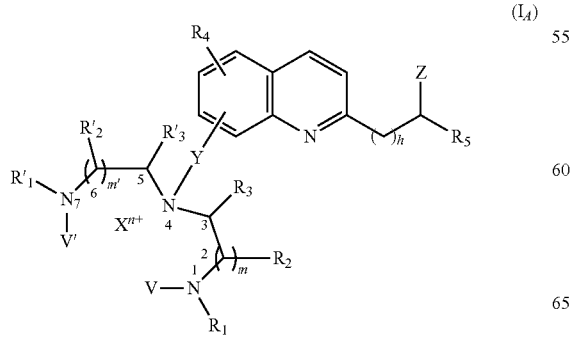

(I_A)

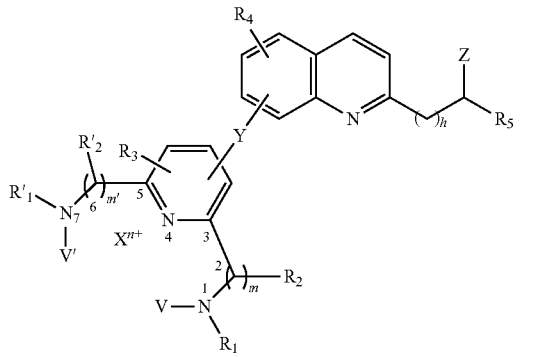

(I_B)

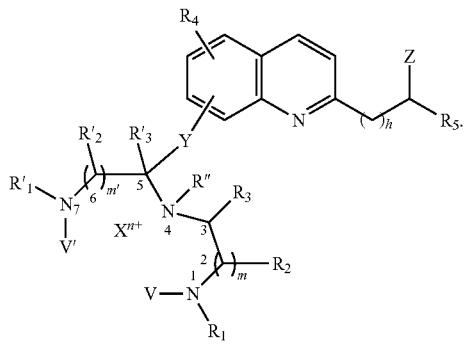

(I_C)

5. A compound as defined according to claim 1, wherein X is a lanthanide.

6. A compound as defined according to claim 1, wherein X is selected among Sm(III), Eu(III), Gd(III), Tb(III), Dy(III) and Ho(III), and preferably Gd(III).

7. A compound as defined according to claim 1, wherein m and m' are equal to 1.

8. A compound as defined according to claim 1, wherein h=0.

9. A compound as defined according to claim 1, wherein the spacer Y comprises a heterocycle having 3 to 5 carbon atoms and 1 or 2 heteroatoms selected among O, N or S, said heterocycle being preferably piperazine, piperidine or pyrazoline.

10. A compound as defined according to claim 1, wherein the spacer Y responds to one of the following formula:

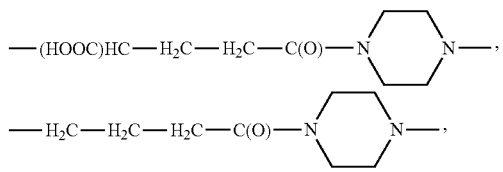

the N heteroatom of said spacer Y being directly linked to the quinoline group.

11. A compound as defined according to claim 1, wherein Z is a —OC(O)R group, in which R is an optionally substituted linear or branched $C_1$-$C_{10}$ alkyl chain.

12. A compound as defined according to claim 1, wherein Z is selected among the following groups

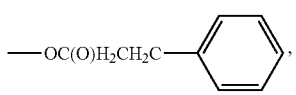

—OC(O)CH₃, —OC(O)CH₂CH₂CH(NH₂)COOH, and —OC(O)CH(NH₂)CH₂CH₂COOH.

13. A compound as defined according to claim 1, responding to the following formula:

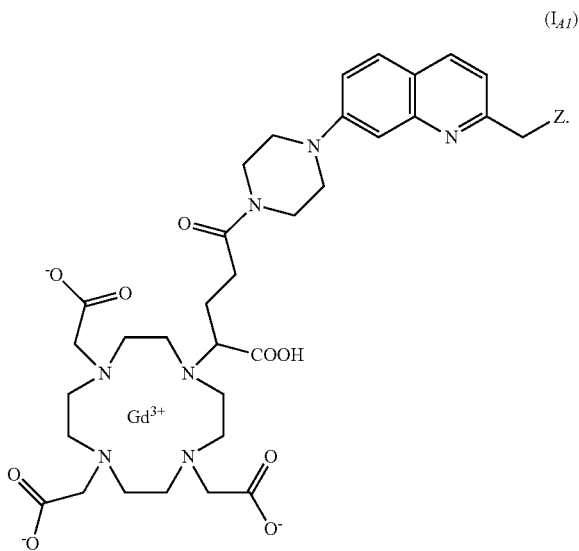

(I_{A1})

14. A method of synthesizing a compound as defined according to claim 1, characterized in that it comprises the following steps:
(i) transformation of an optionally substituted bromoaniline in a bromoquinaldine,
(ii) reaction between the bromoquinaldine obtained in step (i) and an amine,
(iii) amidation of the compound obtained in step (ii) with a protected complex selected among 1,4,7,10-tetraazacyclododecane-1,4,7,10-tetraacetic acid and derivatives, 1,4,7-triazacyclononane-N,N',N"-triacetic acid and derivatives, diethylenetriaminepentaacetic acid and derivatives, pyridine containing triaza-macrocyclic tri-acetate, said complex comprising a metal ion, and
(iv) deprotection of the protected functions of the compound obtained in step (iii) with an acid.

15. A method of synthesizing a compound as defined according to claim 1, characterized in that it comprises a peptide coupling reaction between a quinoline derivative substituted by at least a linear, branched or cyclic $C_1$-$C_{30}$ alkyl or alkoxy chain comprising at least one heteroatom selected among O, N and S, said substituent being directly linked to the quinoline group via its heteroatom O, N or S, and said substituent bearing an amino function, with a complex selected among 1,4,7,10-tetraazacyclododecane-1,4,7,10-tetraacetic acid and derivatives, 1,4,7-triazacyclononane-N,N',N"-triacetic acid and derivatives, diethylenetriaminepentaacetic acid and derivatives, or pyridine containing triaza-macrocyclic triacetate, said complex comprising a metal ion, and said complex also comprising a carboxylic acid function.

16. An aqueous or physiological solution characterized in that it comprises at least one compound as defined according to claim 1.

17. An aqueous or physiological solution as defined according to claim 16, wherein the compound as defined according to claim 1 is present at a concentration ranging from $10^{-5}$ to 10 mol.$L^{-1}$.

18. An aqueous or physiological solution as defined according to claim 16, having a pH of 5 to 9.

19. A method of liberating a Z—H compound, characterized in that it comprises the step of irradiating at least one compound as defined according to claim 1, or at least one aqueous or physiological solution as defined according to claim 16.

20. A method as defined according to claim 19, wherein the irradiating step is carried out under a photonic energy ranging from 10 keV to 20 MeV, and preferably under a photonic energy ranging from 30 to 100 keV.

21. A pharmaceutical composition characterized in that it comprises at least one compound as defined according to claim 1, or at least one aqueous or physiological solution as defined according to claim 16, together with at least one pharmaceutically-acceptable excipient or carrier.

* * * * *